United States Patent [19]

Natako

[11] Patent Number: 4,794,789
[45] Date of Patent: Jan. 3, 1989

[54] RAPID SEDIMENT ANALYZER

[75] Inventor: Tatsuaki Natako, Coralville, Iowa

[73] Assignee: University of Iowa Research Foundation, Iowa City, Iowa

[21] Appl. No.: 129,294

[22] Filed: Dec. 7, 1987

Related U.S. Application Data

[63] Continuation-in-part of Ser. No. 944,177, Dec. 22, 1986, abandoned.

[51] Int. Cl.$^4$ ............................................. G01N 15/04
[52] U.S. Cl. ..................................... 73/61.4; 73/865.5
[58] Field of Search ............. 73/1 B, 1 H, 4 R, 865.5, 73/438, 714, 61.4

[56] References Cited

U.S. PATENT DOCUMENTS 3,788,146  5/1972  Hartman ........................... 73/432 R
3,896,660 12/1973  Valentyik .......................... 73/61.4
4,630,478  6/1984  Johnson ............................. 73/299
4,658,829  4/1987  Wallace ............................. 128/672

FOREIGN PATENT DOCUMENTS 0890157 12/1981  U.S.S.R. ............................ 73/61.4

Primary Examiner—Stewart J. Levy
Assistant Examiner—Robert R. Raevis
Attorney, Agent, or Firm—Ferris M. Stout

[57] ABSTRACT

The Rapid Sediment Analyzer provides information on the size distribution of a sample of finely divided particulate matter (e.g. sand) by monitoring the weight and the rate with which the particles fall through a column of liquid (e.g. water). A digital computer connected to the Analyzer reports the particle size distribution directly.

4 Claims, 2 Drawing Sheets

RAPID SEDIMENT ANALYZER

This is a continuation-in-part of Ser. No. 944,177, filed Dec. 22, 1986, now abandoned.

BACKGROUND OF THE INVENTION

1. Field of the Invention

This invention is in the field of instruments which determine the distribution of particle fall velocities and their sizes by measuring the rate at which solid particles of different sizes fall through a liquid, the specific gravity of which is less than the specific gravity of the particles.

2. The Prior Art

The range of particle sizes in a material is often crucial to the use of the material. For example, the strength of concrete depends critically on the size distribution of the sand used; pigments must be ground to a certain maximum size to be useful in paints; the size distribution of the sand on a river or ocean bottom tells the hydraulic engineer much about currents in the river or ocean, and so forth.

Traditionally, a particle-size analysis is done by sieving a sample through a series of sieves of progressively finer mesh, which enables one to report that, say, 20% of the sample was retained on a 50 mesh screen, 30% of what passed through was retaining on a 140 mesh screen, and so forth. Graduated sieve analysis, however, is prone to error as the finer mesh screens tend to clog. The sieve data are necessarily discontinuous, being dependent on the number of screens and the graduations of mesh used. It is a slow, tedious, labor-intensive process.

Improvements over the graduated sieve method involve determining the time it takes for particles to fall through a column of liquid, typically water. Assuming that the particles are of uniform specific gravity greater than the specific gravity of the liquid, a large particle will fall faster than a small one. It will do so because the drag force and the force of gravity acting on, for example, a sphere, are balanced during the settling process. The drag force is proportional to the product of the square of the diameter of the sphere and the square of the fall velocity; while the force of gravity is proportional to the cube of the diameter. Therefore, the fall velocity if proportional to the square root of the diameter, meaning that a large particle falls faster than a small one.

Consider a settling tube with a sensitive pressure sensor near its bottom. Fill it with water, and add a sample of particles. The sensor will sense a pressure comprising three components:

(a) the pressure equivalent to the initial pressure head of water above the sensor;

(b) the additional pressure representing the volume of water displaced by the sample, and possibly added with the sample;

(c) The additional pressure caused by the apparent weight of the sample in water.

As particles settle past the sensor, pressure component (c) decreases progressively until, after all of the particles have settled to the bottom, it becomes zero. The time record of the changing process while the particles are falling is a measure of the time of fall, and thereby of the changing sizes of the particles as they settle past the sensor. In principle, the rate of fall of the particles, and their weight and volume, and therefore the specific gravity of the particles, can be extracted from (a), (b), and (c).

The actual situation is not quite that straight-forward. The difficulty is that components (b) and (c) are a tiny fraction of component (a). If it is to provide sufficient sensitivity to detect component (c), the sensor must somehow be set to zero when the settling tube is filled.

Although many configurations have been proposed to this end, none has yet provided for the collection and use of all the information embedded in (a), (b), and (c). An example of the prior art is the design taught by Hartman, in U.S. Pat. No. 3,788,146.

The Hartman patent provides a settling tube with a "compensation pipe 2" parallel to it, and connected to the settling tube by a sensitive pressure transducer (Hartman calls it a "pressure difference pick-up") at its bottom end. The transducer measures the differential pressure between the settling tube and the compensation pipe at a point just above the bottom of the settling tube. In one configuration (Hartman's FIG. 2), just below the top of the settling tube a "connecting pipe" connects the settling tube and the compensation pipe so that the water level is the same in each. Hartman provides a "throttle", not a cut-off valve, in the connecting pipe; the connecting pipe remains open throughout the measurement. The fact that Hartman's connecting pipe is not sealed off during the measurement process is crucial to understanding why the sediment analyzer of this invention is a major improvement to the art.

When the operator adds his sample to Hartman's settling tube, the liquid level in the tube rises, proportionately to the water displaced by the sample, and the transducer records this increment. At the instant of adding the sample, the pressure increment at the pressure transducer is further enhanced by the increased density of the fluid in the settling tube, a consequence of the sample suspended in it. At this instant, Hartman's transducer records components (b) and (c) as defined above. But flow th the throttled "connecting pipe" into the compensation pipe quickly restores an equal level in the settling tube and in the compensation pipe. Information about the weight of the sample and its volume is effectively erased when the two liquid levels are equalized. As a consequence, each sample must be carefully weighed before each test, a requirement which can become burdensome when hundreds of samples are to be tested.

A need therefore exists for a liquid column particle size measuring instrument which will povide analyses of particle size distributions in real time without the requirement that each sample be individually weighed.

DESCRIPTION OF A PREFERRED EMBODIMENT

Figure 1:
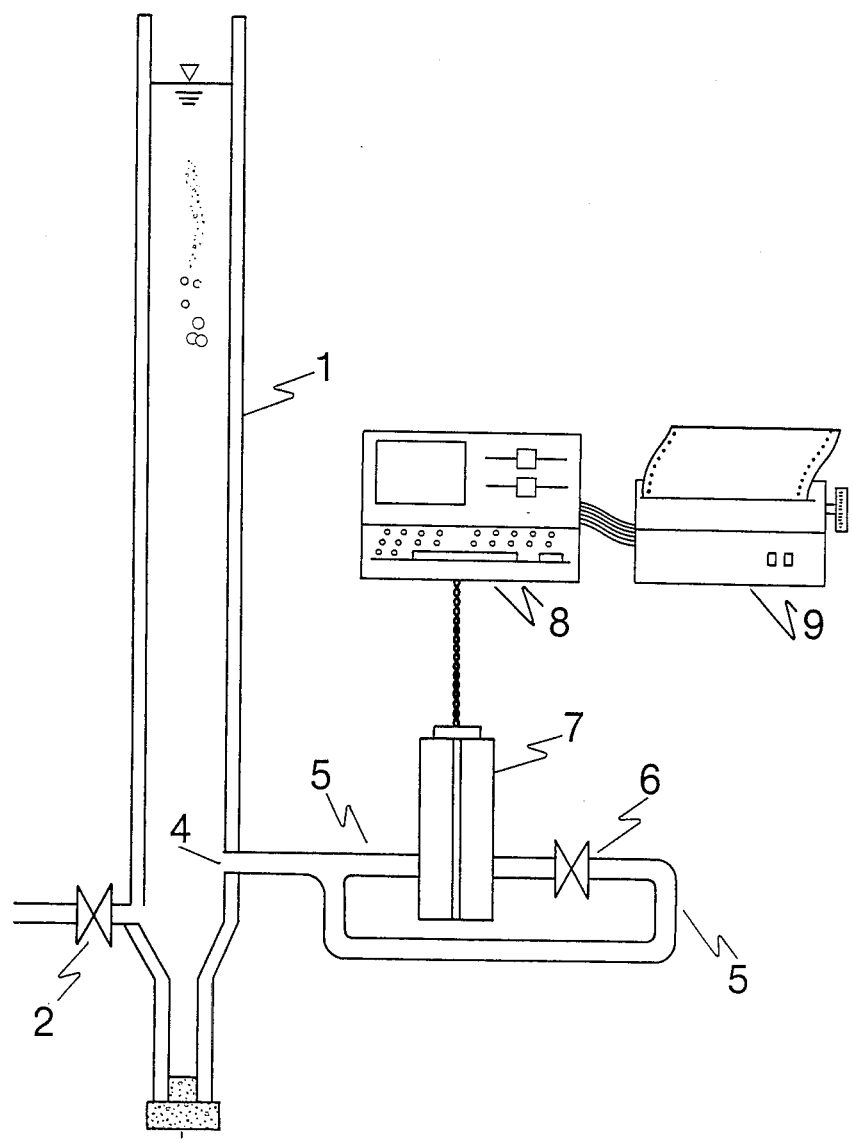
FIG. 1 is a schematic sketch of a preferred embodiment of the Rapid Sediment Analyzer.

FIG. 1 shows a preferred embodiment of the invention. Settling tube 1 may be of any material, although transparent plastic is preferred for convenience. A length of about one meter is covenient and provides time enough for particle sizes to be separated while they fall. Drain valve 2 is useful for draining out water.

Drain plug 3 in the bottom of the tube allows the settled sample to be emptied.

Fluid in settling tube 1 communicates through port 4 in the side of, and somewhat above the bottom of the settling tube, and through piping 5, to both sides of differential pressure transducer (DPT) 7. In this preferred embodiment the DPT has a full-scale range of about 0.0125 psi, or about a third of an inch of water. By means of valve 6, the back side of the DPT can be isolated from the fluid in the settling tube. It is essential that valve 6 be absolutely leak tight.

A microcomputer 8, using a program suitably calibrated, converts DPT readings to a particle size distribution and prints its results out on printer 9.

Figure 2:
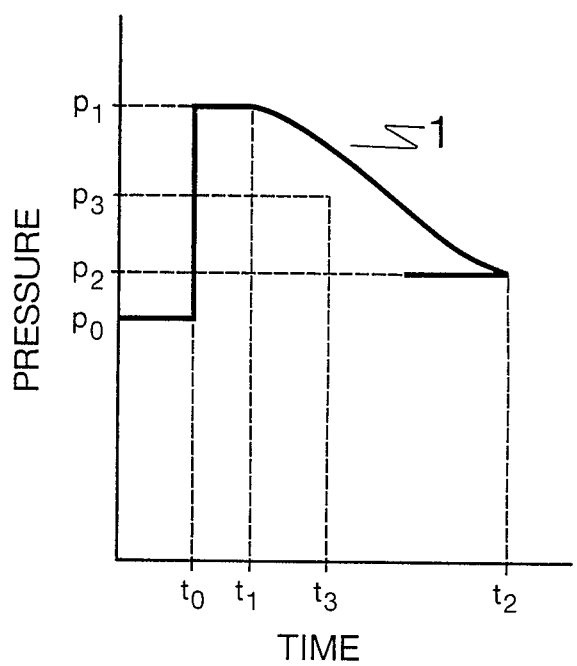
FIG. 2 is an idealized graph of a typical chronological record of pressure recorded during a run of the Rapid Sediment Analyzer.

Please refer now to FIG. 2, a graph of the output of the DPT during a typical particle size analysis. The operator has opened valve 6 and has filled the settling tube with a liquid, let us say water. The pressure at port 4 is proportional to the height of the water in the tube above the port—what we referred to above as component (a). But since, with valve 6 open, the DPT senses exactly the same pressure on its back side as on its front side, its output is zero. On the graph of FIG. 2, we call this pressure $P_o$:

$$p_o = 0 \quad (1)$$

The operator closes valve 6; the DPT output is still $p_o$.

At $t = t_o$ the operator dumps a sample, all at once, into the top of the settling tube. Pressure at port 4 of the settling tube immediately increases because of both component (b) (the weight of the water displaced by the sample), and component (c) (the apparent weight of the sample in the water). The DPT accordingly registers an unchanging output, which we shall refer to as $p_1$:

$$p_1 = p_o + \partial_w(V/a) + (\partial_m - \partial_w)(V/A) = p_o = \partial_m) \quad (2)$$

wherein $\partial_w$ = specific weight of water, $\partial_m$ = specific weight of the sediment sample, V = volume of the sediment sample, and A = the cross-section area of the settling tube.

The particles in the sample immediately begin to fall down the settling tube, large particles rapidly, small particles more slowly. Until the first, largest particle falls past port 4, the DPT senses no pressure change; its output remains at $p_1$ (FIG. 2).

At $t_1$, as the first particle settles past port 4, the specific weight of the column of water and sediment mixture above the port is diminished by the apparent weight (the weight in water) of the particle. The DPT, sensing this change, decreases its output. The DPT output continues to decrease with time as more, and smaller, particles settle past port 4, providing a more or less sloping line or curve (1 on the graph in FIG. 2), until, at $t_2$, the smallest particle has settled past port 4. Thereafter the DPT output remains constant at $p_2$. $p_2$ reflects the additional pressure in the settling tube caused by the volume of water displaced by the dry sample—what was referred to above as component (b):

$$P_2 = p_o + \partial_w(V/A) \quad (3)$$

Embedded in the sloping part of the pressure/time curve,—that is, the section marked 1 in FIG. 2—is the information sought on particle size distribution. It is easy to see that the curve would be a vertical line, or nearly so, if the particles were all of a size, because they would settle past port 4 in a group. If the sample were a mixture of two different sizes of particles, the line would have a step-like shape; and so forth.

W, the weight of the sample analyzed, is, from (1) and (2), $$W = \partial_m V = A(p_1 - p_o) = A_p{}^1 \quad (4)$$

V, the volume of the sample, is, from (1) and (3), $$W = \partial_m V = A(p_1 - p_o) = Ap_1 \quad (4)$$

V, the volume of the sample, is, from (1) and (3)

$$V = A(2 - p_o)/\partial_w = Ap_2/\partial_w \quad (5)$$

From (4) and (5) we can express the specific gravity of the sediment sample, M:

$$m = \partial_m/\partial_w = (A_2/V)/Ap_2/V = p_1/p_2 \quad (6)$$

The fall velocity of any sediment particle size, w, can be derived from $$w = Ge/(t - t_o): t_2 < t < t_2 \quad (7)$$

wherein $H_4 = H_o + (V/A) =$ the actual fall distance in the settling tube, in which $H_{oo}$ is the distance between port 4 and the surface of the water before the sample was introduced into the settling tube; and $V/A =$ the increase in water level attributable to the sample volume. Therefore, the fall velocities of the largest and smallest particles, $W_{max}$ and $W_{min}$, obtained from (7), are $$W_{max} H_4/(t_2 - t_o) \quad (8)$$

and $$W_{min} = H_4/(t_2 - t_o) \quad (9)$$

The fall velocity $w_3$, which corresponds to time $t = t_3$ ($t_1 < t_3 < t_2$) can, therefore, be gotten from (7) by $$W_3 = H_4/(t_3 - t_o) \quad (10)$$

A fraction $F(w_3)$ for which the fall velocity, w, is larger than $w_3$, can be derived from $$F(w_3: w > w_3) = (p_1 - p_3)/(p_1 - p_2) \quad (11)$$

To abstract from curve 1 of FIG. 2 useful information in terms of particle sizes one proceeds as follows.

The fraction $F(w < w_3)$ for which w is smaller than $w_3$ is given by $$F(w < w_3) = 1 - F(w_3) \quad (12)$$

The next tast is to use the frequency distribution of fall velocities we have just derived to obtain a frequency distribution of particle sizes. One method for accomplishing this task is to calculate the diameter of a fictional spherical particle which would fall at the same rate as the real particle. The result of this calculation we shall refer to as the "apparent fall diameter" of the particle. To do this we proceed as follows.

The fall velocity, w, of a sphere of diameter d is given by $$w^2 = (4gd/3C_d)(\partial_m - \partial_w)/\partial_w \quad (13)$$

wherein
g = the gravitational constant,
$\partial_m$ = the specific weight of the sediment, and
$C_D$ = drag coefficient.

But note that $C_D$ is a function of Reynold's number, Re. Re = wd/#(T), wherein # = the kinematic viscosity of the liquid and T = the temperature of the liquid.

We estimate a particle size for a known value of the fall velocity w by a process of trial and error, using the following procedure: First we select a reasonable particle size. Then for a known #(T) we calculate the Reynolds number and derive the drag coefficient $C_D$. Next, using (13), we calculate the particle's apparent fall diameter d, and compare it to the estimated value of d. If the two are not close, we estimate a new d and repeat the procedure, continuing thus until the two values of d are satisfactorily congruent.

The procedure outlined is recursive, and thus lends itself nicely to an algorithm for a digital computer program. We have developed such a program for IBM(TM)-compatible PC's. The program not only produces virtually continuous cumulative distributions of sediment fall velocities and fall diameters, but also useful statistical quantities such as medium size of the particles, geometrical standard deviation, and skewness factors of the particle size distribution.

The examples and embodiments of the invention have been recited here to illustrate and explain the invention. They are not to be construed as limiting of the invention; the scope of the invention is as set forth in the Claims.

What is claimed is:

1. A method for determining fall velocities of particles settling in a settling tube which comprises the steps of
    providing the settling tube with a port near its bottom, the port being connected to both sides of a differential pressure transducer, one side of the differential pressure transducer being isolatable from the settling tube by means of a valve,
    filling the settling tube with a liquid while the valve is open,
    closing the valve,
    introducing a sample of dry particulate matter, the specific gravity of which is greater than that of the liquid in the settling tube, into the top of the settling tube, and
    recording as a function of time the changing output of the differential pressure transducer as the particulate matter falls past the port in the settling tube, whereby the weight and volume of the sample, and the fall velocity and size distribution of the particles in the sample, are determined.

2. In an apparatus for measuring the sedimentation characteristics of solid particles suspended in a liquid which comprises a settling tube having a bottom and an open top, a valved drain in the bottom of the settling tube, a port between the top and the bottom, and a first pipe fluidly connecting the port in the settling tube to a first sensing port on a differential pressure transducer, the improvement comprising
    a second pipe connecting the first pipe to a second sensing port on the differential pressure transducer; and,
    a shut-off valve in the second pipe.

3. In an apparatus for measuring the sedimentation characteristics of solid particles suspended in a liquid which comprises a settling tube having a bottom and an open top, a valved drain in the bottom of the settling tube, a port between the top and the bottom, and a first pipe fluidly connecting the port in the settling tube to a first sensing port on a differential pressure transducer, the improvement comprising
    a second pipe fluidly connecting the first pipe to a second sensing port on the differential pressure transducer,
    a shut-off valve in the second pipe, and
    a computer program and a computer which is compatible with the program electrically connected to the output of the differential pressure transducer, whereby the output of the differential pressure transducer is converted into particle fall velocities and apparent fall diameters.

4. A method for determining the distribution of fall velocities and apparent fall diameters of particulate matter, the particulate matter comprising particles of different sizes, the method comprising the steps of
    providing a settling tube with a port near its bottom, the port being connected to both sides of a differential pressure transducer, one side of the differential pressure transducer being isolatable from the settling tube by means of a valve,
    filling the settling tube with a liquid of specific gravity less than that of the particulate matter which is to be tested, while the valve is open,
    closing the valve,
    introducing a sample of the particulate matter into the top of the settling tube,
    connecting the output of the differential pressure transducer through appropriate circuitry to a digital computer, and
    By means of a computer program, converting the output of the differential pressure transducer into
    (a) the weight and volume of the particulate matter,
    (b) the specific gravity of the particulate matter,
    (c) the distribution of fall velocities, and
    (d) from (c), calculating the distribution of the apparent fall diameters of the particulate matter.

* * * * *